(12) United States Patent
Davis et al.

(10) Patent No.: US 6,387,715 B1
(45) Date of Patent: May 14, 2002

(54) INTEGRATED CIRCUIT DEFECT DETECTION VIA LASER HEAT AND IR THERMOGRAPHY

(75) Inventors: Brennan V. Davis; Rama R. Goruganthu; Jeffrey D. Birdsley; Michael R. Bruce; Rosalinda M. Ring, all of Austin, TX (US)

(73) Assignee: Advanced Micro Devices, Inc., Sunnyvale, CA (US)

( * ) Notice: Subject to any disclaimer, the term of this patent is extended or adjusted under 35 U.S.C. 154(b) by 0 days.

(21) Appl. No.: 09/409,975

(22) Filed: Sep. 30, 1999

(51) Int. Cl.[7] ............................................... H01L 21/66
(52) U.S. Cl. ...................................................... 438/16
(58) Field of Search .............................. 438/4, 5, 7, 14, 438/16; 356/213, 216, 237; 250/307

(56) References Cited

U.S. PATENT DOCUMENTS 5,021,362 A * 6/1991 Chlipala ........................ 438/7
5,781,017 A   7/1998 Cole, Jr. et al.
5,821,549 A * 10/1998 Talbot et al. ................ 250/307

OTHER PUBLICATIONS

McDonald, J. et al., "Microthermal Imaging in theInfrared", Electronics Cooling (http://www.electronic–cooling.com), Jan. 1997.*

* cited by examiner

Primary Examiner—Keith Christianson

(57) ABSTRACT

Defect detection for post-manufacturing analysis of an integrated circuit die is enhanced via a method and system that use IR thermography to detect defects in circuitry within the die. According to an example embodiment of the present invention, substrate is removed from an integrated circuit die and a target region is exposed. A portion of the target region is heated with an infrared (IR) laser beam, and the die is imaged using IR thermography. The image is compared with a reference image, and damage to the integrated circuit is detected therefrom.

20 Claims, 2 Drawing Sheets

INTEGRATED CIRCUIT DEFECT DETECTION VIA LASER HEAT AND IR THERMOGRAPHY

FIELD OF THE INVENTION

The present invention relates generally to semiconductor devices and their fabrication and, more particularly, to semiconductor devices and their manufacture involving techniques for analyzing and debugging circuitry within an integrated circuit.

BACKGROUND OF THE INVENTION

The semiconductor industry has recently experienced technological advances that have permitted dramatic increases in circuit density and complexity, and equally dramatic decreases in power consumption and package sizes. Present semiconductor technology now permits single-chip microprocessors with many millions of transistors, operating at speeds of hundreds of millions of instructions per second to be packaged in relatively small, air-cooled semiconductor device packages. A by-product of such high-density and high functionality in semiconductor devices has been the demand for increased numbers of external electrical connections to be present on the exterior of the die and on the exterior of the semiconductor packages which receive the die, for connecting the packaged device to external systems, such as a printed circuit board.

As the manufacturing processes for semiconductor devices and integrated circuits increase in difficulty, methods for testing and debugging these devices become increasingly important. Not only is it important to ensure that individual chips are functional, it is also important to ensure that batches of chips perform consistently. In addition, the ability to detect a defective manufacturing process early is helpful for reducing the number of defective devices manufactured.

Traditionally, integrated circuits have been tested using methods including directly accessing circuitry or devices within the integrated circuit. In addition, many methods require the circuit to be powered. Directly accessing the circuitry is difficult for several reasons. For instance, in flip-chip type dies, transistors and other circuitry are located in a very thin epitaxially-grown silicon layer in a circuit side of the die. The circuit side of the die is arranged face-down on a package substrate. This orientation provides many operational advantages. However, due to the face-down orientation of the circuit side of the die, the transistors and other circuitry near the circuit side are not readily accessible for testing, modification, or other purposes. Therefore, access to the transistors and circuitry near the circuit side is from the back side of the chip.

Since access to the transistors and circuitry in flip-chips is generally from the back side of the device, it is often necessary to mill through the back side and probe certain circuit elements in order to test the device. Milling through the back side is often difficult and time consuming. Moreover, circuitry and devices in integrated circuits including flip-chips and others, may potentially be damaged by milling processes. The difficulty, cost, and destructive aspects of existing methods for testing integrated circuits are impediments to the growth and improvement of semiconductor technologies.

SUMMARY OF THE INVENTION

The present invention is directed to a method and system for post-manufacturing analysis of a semiconductor device involving the imaging and detection of defects in the device using infrared (IR) thermography. The present invention is exemplified in a number of implementations and applications, some of which are summarized below.

According to an example embodiment of the present invention, substrate is removed from an integrated circuit die and a target region is exposed. A portion of the target region is heated with an infrared (IR) laser beam, and the target region is imaged using IR thermography. The image of the target region is compared to a reference image, and circuit damage is determined via the comparison.

The above summary of the present invention is not intended to describe each illustrated embodiment or every implementation of the present invention. The figures and detailed description which follow more particularly exemplify these embodiments.

BRIEF DESCRIPTION OF THE DRAWINGS

The invention may be more completely understood in consideration of the following detailed description of various embodiments of the invention in connection with the accompanying drawings, in which.

Figure 1:
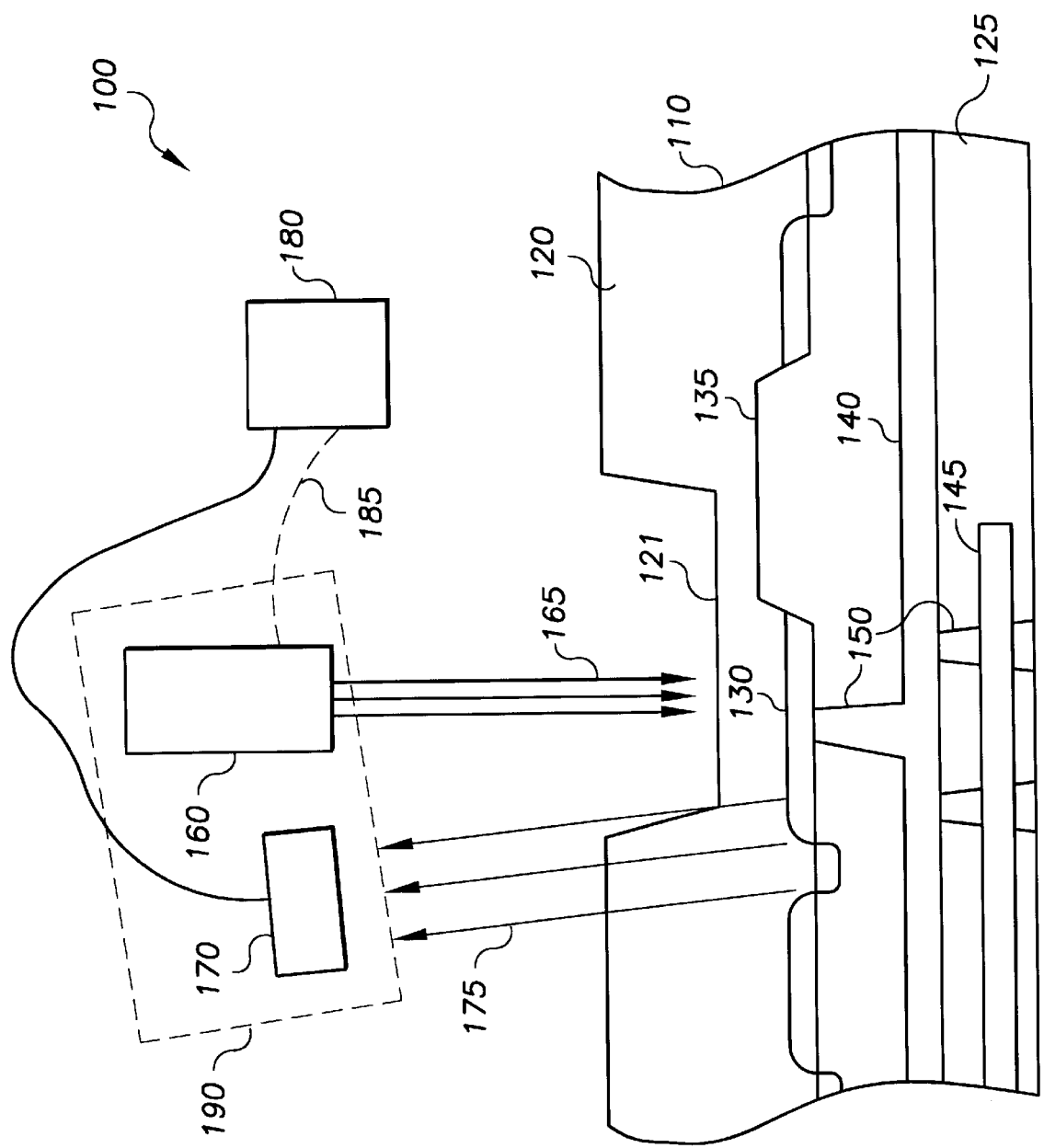
FIG. 1 shows a system for analyzing an integrated circuit die, according to an example embodiment of the present invention.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention as defined by the appended claims.

DETAILED DESCRIPTION

The present invention is believed to be applicable to a variety of different types of semiconductor devices, and the invention has been found to be particularly suited for flip-chip and other integrated circuit devices requiring or benefiting from post-manufacturing analysis involving defect detection. While the present invention is not necessarily limited to such devices, various aspects of the invention may be appreciated through a discussion of examples using this context.

In connection with an example embodiment of the present invention, IR thermography is used to create an image of circuitry within an integrated circuit die. The image of the circuitry is then compared with a reference image. Variances between the created image and the reference image indicate defects. In this manner, defective portions of integrated circuit dies can be detected.

According to a more particular example embodiment of the present invention, FIG. 1 shows a system 100 for analyzing a portion of an integrated circuit die 110 for defects. The die 110 has a back side 120 opposite circuitry in a circuit side 125. Source/drain regions 130 are coupled by vias 150 to metal layers 140 and 145. Trench isolation region 135 separates devices within the die. System 100 is adapted to remove substrate from the back side 120, form a target region 121, and capture an image of circuitry in the target region using IR thermography.

The substrate removal can be accomplished in various manners, such as by using a focused ion beam (FIB) or other ion bombardment device, a laser etching device, or a chemical mechanical polishing arrangement. FIG. 1 shows the target region 121 formed in the back side 120 of the die, and having a portion of substrate remaining over the circuitry in the circuit side 125. In alternative embodiments, the target region is formed in other regions of the die, such as by removing substrate to expose another portion of the back side, or by exposing circuitry in the die, and this can include removing a some or all of a layer of circuitry. The target region could also be formed in the circuit side 125 of the die, wherein access to the target region is via the circuit side 125. In addition, the target region can be selected for several reasons, such as for performing a systematic analysis of the die for defects, or because the target region includes circuitry suspected of being defective.

Once the target region has been exposed, an IR laser source 160 is used to direct IR laser beam 165 at the target region 121 and to heat circuitry in the circuit side 125. The heat is transferred within the device to surrounding circuitry by way of the vias 150, source/drain regions 130, metal interconnects 140, and other circuitry in the die. In one particular embodiment, the laser transfers heat to a portion of the metal interconnects 140, and the heat is readily transferred by conduction to other portions of the interconnects 140. An imaging device 170 is used to capture the image 175 from the heated circuitry. For example, a laser-scanning microscope or an IR camera can be used to capture the image. The laser source 160 and the imaging device 170 can also be configured in a single arrangement 190. The image is then used and compared to a reference image at a computer arrangement 180. Alternatively, the image can be arranged on a display (not shown) and compared by a human operator. The reference image may, for example, be obtained by creating an image from a non-defective die using IR thermography or other imaging method, or by using the design layout of the circuitry in the die. Using the comparison, differences between the image captured from the heated circuitry and the reference are detected as defects in the die 110.

Differences between the captured IR image and the reference image may result from defects such as opens, shorts, or voids in the circuitry. Heat applied to circuitry is transferred along the circuitry via conduction. However, when heat is applied to circuitry such as the interconnect that includes an open circuit portion, the heat is not transferred along the circuit beyond the open portion. When IR thermography is used to image the die, the image of portions of circuitry beyond the open is different than the reference image. Alternatively, when a portion of the circuitry includes a short, heat applied to the circuitry is transferred to the additional circuitry coupled to the short. The image including the additional heated circuitry is different than the reference image.

Heating with an IR laser has several advantages. For instance, the IR laser can be used without generating electron-hole pairs in the integrated circuit die to which it is being applied. This is advantageous because the generation of electron-hole pairs can be a hindrance to imaging the device due to current generated in the device by the electron-hole pairs. Another advantage of this method of using an IR laser is that defects can be detected in a relatively simple and inexpensive manner that does not necessarily require electrically coupling the die to outside power sources or to measurement devices. In addition, the circuitry can be imaged without necessarily accessing the circuitry directly, and can be done through substrate located over the circuitry.

Figure 2A:
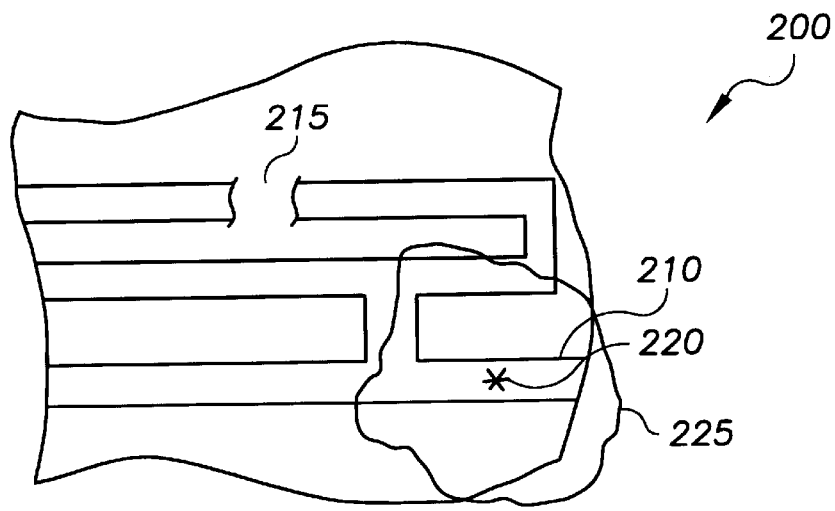
FIGS. 2A–2C show a portion of an integrated circuit device undergoing analysis, according to another example embodiment of the present invention.
Figure 2B:
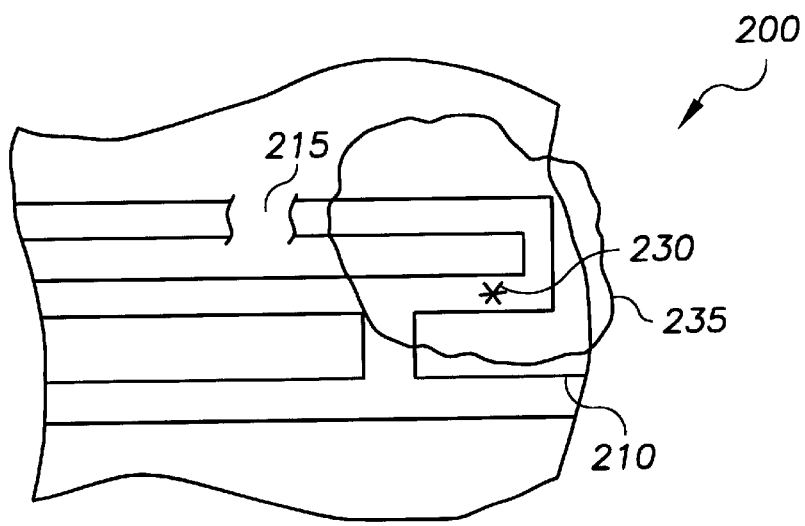
Figure 2C:
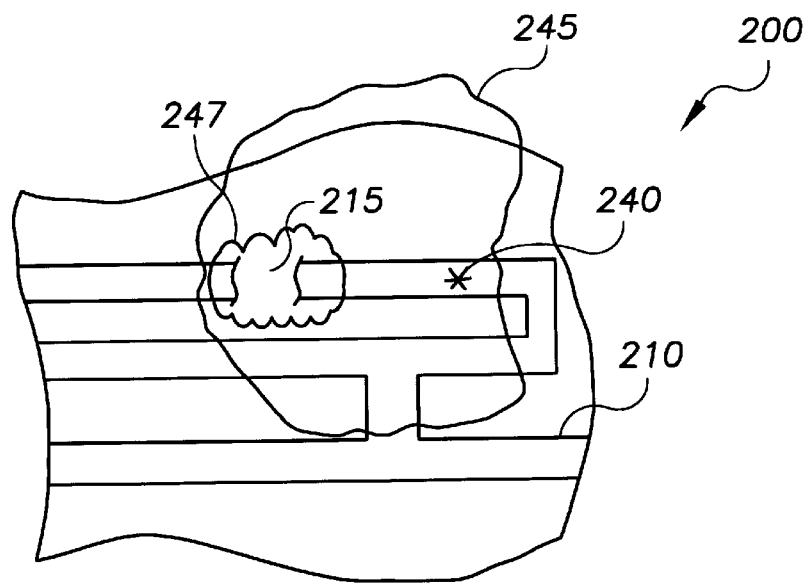

FIGS. 2A–2C show a portion of circuitry 210 in an integrated circuit die 200 undergoing defect analysis, according to another example embodiment of the present invention. The circuitry 210 has an open 215 and is heated via an IR laser at a series of target spots for defect analysis. An IR laser in a spot mode is directed at a first target spot 220 in FIG. 2A. The IR laser heats target circuitry 225 near the target spot 220, including heating by conduction target circuitry not included in the target spot 220. The die is then imaged using IR thermography and compared with a reference image. Since the open 215 is not included in the target circuitry, it is not detected. In response to not detecting a defect, the IR laser is adjusted and used to direct an IR laser beam at a second target spot 230 in FIG. 2B. Heat is transferred via the IR laser to the target spot 230 and via conduction to other target circuitry 235 and the die is re-imaged using IR thermography. When compared to a reference, the target circuitry 235 does not show the defective open 215. Again in response to not detecting a defect, the IR laser is adjusted and used to direct an IR laser beam at a third target spot 240 in FIG. 2C. Heat is transferred via conduction to other target circuitry 245 which is imaged using IR thermography. However, due to the open 215, a portion 247 of the target circuitry 245 is not heated as it would be had there been no open. The image shows the unheated portion, and when compared to a reference image, the open is detected. In this manner, an IR laser in spot mode can be used to locate defective circuitry in the die.

In one particular example application, a network of highly heat-conductive structures in an integrated circuit die is analyzed for defects. A portion of the heat-conductive structure is spot-heated using an IR laser. The conductivity of the structure causes the heat generated by the IR laser to spread throughout the structure. An IR image of the structure is generated, and defects are detected therefrom.

In another example embodiment of the present invention, the IR laser is used in a scan mode to image a portion of the circuitry and to detect defects in the die using IR thermography as described in connection with FIGS. 1 and 2A–2C. Scanning the die with the laser can be used to heat a greater portion of the die than would be heated by directing the laser at a single spot. The scan mode can be used to detect defects directly, or can be used in conjunction with the spot mode. For instance, the scan mode can be used to generally locate a defect. Once a defect is generally located, the laser can be directed at a target spot using a spot mode to more specifically identify and locate the defect.

According to another example embodiment of the present invention, and using either or both of the spot mode and the scan mode applications of the IR laser described above in connection with FIGS. 2A–2C, the IR laser is adjusted in response to the compared images using a computer arrangement. As shown in FIG. 1, the computer arrangement 180 is optionally coupled via coupling 185 to the laser source 160. The images captured at imaging device 170 are used by the computer 180 and compared to a reference image. In response to the comparison, the computer 180 sends a signal to the laser source 160 and the application of the laser beam is adjusted. For example, the computer 180 can send a signal to the laser source 160 to apply the laser in a scan mode or a spot mode, to direct the laser at a different target region in the die 110, or to adjust the intensity of the laser.

While the present invention has been described with reference to several particular example embodiments, those skilled in the art will recognize that many changes may be made thereto without departing from the spirit and scope of the present invention, which is set forth in the following claims.

What is claimed is:

1. A method for detecting circuit damage in an integrated circuit die, the method comprising:

removing substrate from the die and exposing a target region;

heating a portion of the target region with an infrared (IR) laser beam;

imaging the target region via IR thermography; and comparing the image of the target region to a reference image and determining therefrom circuit damage.

2. The method of claim 1, wherein comparing the image of the target region to a reference image and determining therefrom circuit damage comprises:

comparing the image of the target region to a reference image, and in response to not detecting circuit damage, heating another portion of the target region and re-imaging the target region; and comparing the re-imaged target region to the reference image and detecting therefrom circuit damage.

3. The method of claim 2, wherein comparing the image, heating another portion of the target region, and re-imaging the target region are repeated until a defect has been detected.

4. The method of claim 1, wherein heating a portion of the target region with an infrared (IR) laser beam includes using the laser beam in a spot mode.

5. The method of claim 1, wherein heating a portion of the target region with an infrared (IR) laser beam includes using the laser beam in a scan mode.

6. The method of claim 1, wherein the integrated circuit die has circuitry in a circuit side opposite a back side, and wherein the target region includes suspect circuitry.

7. The method of claim 6, wherein the exposed target region includes substrate over the circuitry.

8. The method of claim 6, wherein removing substrate from the die includes removing substrate from the back side of the die.

9. The method of claim 6, wherein removing substrate from the die includes removing substrate from the circuit side of the die.

10. The method of claim 1, wherein heating a portion of the target region includes directing the IR laser beam at a first portion and heating other portions of the target region by heat conduction emanating from the first-recited portion.

11. The method of claim 10, wherein comparing the image of the target region to a reference image and determining therefrom circuit damage includes detecting a defect in a portion of the target region by determining the portions of the target circuitry that are heated by the heat conduction.

12. The method of claim 1, wherein comparing the image of the target region to a reference image and determining therefrom circuit damage includes using a computer.

13. The method of claim 1, wherein the reference image is developed by using a non-defective integrated circuit die and imaging the die using IR thermography.

14. The method of claim 1, wherein the reference image is developed using the design layout of the integrated circuit die.

15. A system for detecting circuit damage in an integrated circuit die, the system comprising:

means for removing substrate from the die and exposing a target region;

means for heating a portion of the target region with an infrared (IR) laser beam;

means for imaging the target region via IR thermography; and means for comparing the image of the target region to a reference image and determining therefrom circuit damage.

16. A system, according to claim 15, wherein the means for removing substrate from the die and exposing a target region includes at least one of: a focused ion beam (FIB), a laser etching device, an ion bombardment device, and a chemical-mechanical polishing arrangement.

17. A system, according to claim 15, wherein the means for heating a portion of the target region with an infrared (IR) laser beam includes at least one of: an IR laser and a laser scanning microscope.

18. A system, according to claim 15, wherein the means for imaging the target region via IR thermography includes at least one of: a laser scanning microscope and an IR camera.

19. A system, according to claim 15, wherein the means for comparing the image of the target region to a reference image and determining therefrom circuit damage includes at least one of: a computer, a display, and a computer programmed and adapted to compare images and control the IR laser.

20. A method for detecting circuit damage in an integrated circuit die having circuitry, the method comprising:

using a FIB, removing substrate from the die and exposing a target region;

directing an IR laser at the target region and spot-heating a portion of the target region including target circuitry;

using IR thermography and generating an image of the target circuitry;

using a laser scanning microscope to compare the generated image of the target circuitry to a reference image of the target circuitry; and responsive to detecting discrepancies in the generated image of the target circuitry, detecting circuit damage.

* * * * *